United States Patent
Xu et al.

(10) Patent No.: US 11,739,200 B2
(45) Date of Patent: Aug. 29, 2023

(54) 3-PHENYL-3H-1-BENZOFURAN-2-ONE COMPOUNDS AND COMPOSITIONS COMPRISING THE SAME

(71) Applicant: Milliken & Company, Spartanburg, SC (US)

(72) Inventors: Xiaoyou Xu, Spartanburg, SC (US); Keith A. Keller, Spartanburg, SC (US); Suchitra Datta, Spartanburg, SC (US); Matthew D. Meador, Union, SC (US)

(73) Assignee: Milliken & Company, Spartanburg, SC (US)

( * ) Notice: Subject to any disclaimer, the term of this patent is extended or adjusted under 35 U.S.C. 154(b) by 119 days.

(21) Appl. No.: 17/181,048

(22) Filed: Feb. 22, 2021

(65) Prior Publication Data

US 2021/0171747 A1   Jun. 10, 2021

Related U.S. Application Data

(62) Division of application No. 16/248,929, filed on Jan. 16, 2019, now Pat. No. 10,947,370.

(60) Provisional application No. 62/620,172, filed on Jan. 22, 2018.

(51) Int. Cl.
| | | |
|---|---|---|
| *C08L 23/06* | (2006.01) |
| *C08K 5/134* | (2006.01) |
| *C08K 5/526* | (2006.01) |
| *C07D 307/83* | (2006.01) |
| *C08K 5/05* | (2006.01) |
| *C08K 5/07* | (2006.01) |
| *C08K 5/098* | (2006.01) |
| *C08K 5/1535* | (2006.01) |
| *C08K 5/524* | (2006.01) |
| *C08L 23/12* | (2006.01) |
| *C08K 5/00* | (2006.01) |

(52) U.S. Cl.
CPC ............. *C08L 23/06* (2013.01); *C07D 307/83* (2013.01); *C08K 5/05* (2013.01); *C08K 5/07* (2013.01); *C08K 5/098* (2013.01); *C08K 5/1345* (2013.01); *C08K 5/1535* (2013.01); *C08K 5/524* (2013.01); *C08K 5/526* (2013.01); *C08L 23/12* (2013.01); *C08K 5/005* (2013.01)

(58) Field of Classification Search
CPC ......... C08L 23/06; C08L 23/12; C08K 5/098; C08K 5/524; C08K 5/1535; C08K 5/005; C08K 5/07; C08K 5/526; C08K 5/1345; C08K 5/05; C07D 307/83
USPC ........................................ 524/111
See application file for complete search history.

(56) References Cited

U.S. PATENT DOCUMENTS

| | | | |
|---|---|---|---|
| 4,325,863 A | | 4/1982 | Hinsken et al. |
| 5,428,162 A | * | 6/1995 | Nesvadba ........... C07F 9/65517 |
| | | | 549/60 |
| 2001/0009939 A1 | | 7/2001 | Laver et al. |

FOREIGN PATENT DOCUMENTS

| | | |
|---|---|---|
| AT | 383 816 B | 8/1987 |
| WO | WO 01/59000 A1 | 8/2001 |
| WO | WO 2006/065829 A1 | 6/2006 |

OTHER PUBLICATIONS

International Search Report for PCT/US2019/013737.
Written Opinion of the International Searching Authority for PCT/US2019/013737.

* cited by examiner

*Primary Examiner* — Hui H Chin
(74) *Attorney, Agent, or Firm* — Robert M. Lanning

(57) ABSTRACT

A 3-phenyl-3H-1-benzofuran-2-one compound is substituted with one or more acyloxy groups comprising 26 or more carbon atoms. A compound comprises two or more 3-phenyl-3H-1-benzofuran-2-one moieties and a second moiety selected from the group consisting of divalent and polyvalent $C_4$-$C_{60}$ hydrocarbon moieties. Each 3-phenyl-3H-1-benzofuran-2-one moiety is covalently bound to an open valence of the second moiety through a linking group selected from the group consisting of a carboxy group and oxyalkylene ester moieties. A composition comprises the 3-phenyl-3H-1-benzofuran-2-one compound described above or the compound described above comprising two or more 3-phenyl-3H-1-benzofuran-2-one moieties.

24 Claims, No Drawings

3-PHENYL-3H-1-BENZOFURAN-2-ONE COMPOUNDS AND COMPOSITIONS COMPRISING THE SAME

CROSS-REFERENCE TO RELATED PATENT APPLICATIONS

This application is a division of co-pending U.S. patent application Ser. No. 16/248,929 filed on Jan. 16, 2019, which application claims, pursuant to 35 U.S.C. § 119(e)(1), priority to and the benefit of the filing date of U.S. Patent Application No. 62/620,172 filed on Jan. 22, 2018, both of which applications are hereby incorporated by reference in their entireties.

TECHNICAL FIELD OF THE INVENTION

This application relates to compounds containing one or more 3-phenyl-3H-1-benzofuran-2-one moieties, compositions comprising such compounds, and the use of such compounds as antioxidants for materials.

BACKGROUND

Synthetic polymers have become ubiquitous in everyday life. For example, thermoplastic polymers are used to produce a variety of durable goods (e.g., home appliances, consumer electronics, furniture, and automobiles), consumable goods, and packaging materials for such goods. To produce such goods and materials, a thermoplastic polymer typically is heated to a temperature above its melting point and molded or otherwise processed using one of a variety of known processes. Further, to increase throughput and improve processability, the thermoplastic polymer typically is heated to a temperature that is well above it melting point. While exposure to such high temperatures has its benefits, such exposure also damages the thermoplastic polymer. The high temperatures can accelerate a variety of oxidative and thermal degradation processes that breakdown certain polymers, which can lead to yellowing and increases in melt flow rates due to breaking of the polymer chains. In other polymers, such as polyethylene, exposure to high heat can cause crosslinking and lead to the formation of gels in the polymer. These negative effects are exacerbated when the polymer is recycled through a production process and encounters multiple melting and cooling cycles.

To combat these degradative process, a variety of antioxidant or stabilizer compounds have been developed for use in thermoplastic polymers. For example, hindered phenol compounds and phosphite compounds frequently are used as stabilizers or antioxidants for thermoplastic polymers. While these compounds work to slow the degradation of the polymer, the industry continues to seek new antioxidants and stabilizers that can improve upon the performance of these materials. Accordingly, others have explored the use of benzofuranone compounds as antioxidants or stabilizers for thermoplastic polymers. These benzofuranone compounds initially showed some promise, but some commercial embodiments of such products were discontinued due to various concerns. Further, other commercially-available forms of benzofuranone compounds exhibited poor solubility in molten thermoplastic polymers or undesirably high extraction from the finished good.

A need therefore remains for compounds that exhibit improved antioxidant activity without the drawbacks exhibited by known compounds. The compounds and compositions described herein are believed to fulfill this unmet need.

BRIEF SUMMARY OF THE INVENTION

In a first embodiment, the invention provides a 3-phenyl-3H-1-benzofuran-2-one compound, wherein the 3-phenyl group is substituted with one or more acyloxy groups comprising 26 or more carbon atoms.

In a second embodiment, the invention provides a compound comprising two or more 3-phenyl-3H-1-benzofuran-2-one moieties and a second moiety selected from the group consisting of divalent and polyvalent $C_4$-$C_{60}$ hydrocarbon moieties, wherein each 3-phenyl-3H-1-benzofuran-2-one moiety is covalently bound to an open valence of the second moiety through a linking moiety selected from the group consisting of a carboxy group and oxyalkylene ester moieties.

In a third embodiment, the invention provides a composition comprising at least one of the above-described compounds and a second component selected from the group consisting of antioxidants, metal salts of fatty acids, and mixtures thereof.

In a fourth embodiment, the invention provides a composition comprising an organic polymer and one of the above-described compounds, one of the above-described compositions, or a mixture thereof.

DETAILED DESCRIPTION OF THE INVENTION

In a first embodiment, the invention provides a 3-phenyl-3H-1-benzofuran-2-one compound. In the compound, the 3-phenyl group is substituted with one or more acyloxy groups. The acyloxy group(s) can be bonded to the 3-phenyl group at any suitable position. Preferably, the acyloxy group(s) are bonded to the 3-phenyl group in the ortho or para position relative to the bond to the 3H-1-benzofuran-2-one moiety. More preferably, the acyloxy group is bonded to the 3-phenyl group in the para position relative to the bond to the 3H-1-benzofuran-2-one moiety. The acyloxy group(s) can comprise any suitable number of carbon atoms. Preferably, the acyloxy group comprises 26 or more carbon atoms. More preferably, the acyloxyl group comprises 30 or more carbon atoms (e.g., 30-90 carbon atoms).

In a preferred embodiment, the 3-phenyl-3H-1-benzofuran-2-one compound conforms to Formula (I)

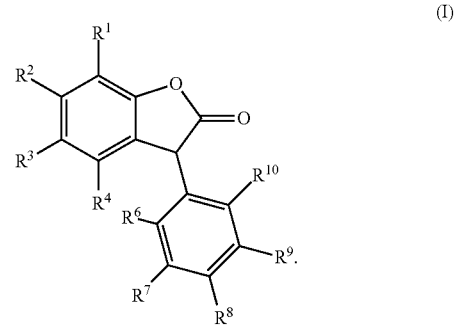

In the structure of Formula (I), $R^1$, $R^2$, $R^3$, and $R^4$ are independently selected from the group consisting of hydrogen, hydroxy, halogens, alkyl groups, substituted alkyl groups, alkoxy groups, substituted alkoxy groups, aralkyl groups, substituted aralkyl groups, alkaryl groups, substituted alkaryl groups, cycloalkyl groups, substituted cycloalkyl groups, alkylamino groups, substituted alkylamino groups, acyloxy groups, and substituted acyloxy groups. Further, adjacent pairs of $R^1$, $R^2$, $R^3$, and $R^4$ can be linked to form a fused benzene ring. In a preferred embodiment, $R^1$, $R^2$, $R^3$, and $R^4$ are independently selected from the group consisting of hydrogen and alkyl groups (e.g., $C_1$-$C_8$ alkyl groups, more preferably $C_1$-$C_4$ alkyl groups). More preferably, $R^1$ and $R^3$ are independently selected alkyl groups (e.g., $C_1$-$C_8$ alkyl groups, more preferably $C_1$-$C_4$ alkyl groups), and $R^2$ and $R^4$ are hydrogen. In such an embodiment, $R^1$ and $R^3$ preferably are tert-butyl groups.

In the structure of Formula (I), $R^6$, $R^7$, $R^8$, $R^9$, and $R^{10}$ are independently selected from the group consisting of hydrogen, halogens, alkyl groups, substituted alkyl groups, alkoxy groups, substituted alkoxy groups, and —$OR^5$. Preferably, at least one of $R^6$, $R^8$, and $R^{10}$ is —$OR^5$. In a preferred embodiment, $R^6$, $R^7$, $R^8$, $R^9$, and $R^{10}$ are independently selected from the group consisting of hydrogen and —$OR^5$, provided at least one of $R^6$, $R^8$, and $R^{10}$ is —$OR^5$. More preferably, $R^6$, $R^7$, $R^9$, and $R^{10}$ are hydrogen, and $R^8$ is —$OR^5$.

The group $R^5$ is selected from the group consisting of —$R^{11}$—$C(O)$—$R^{12}$ and —$C(O)$—$R^{12}$. In a preferred embodiment, $R^5$ is —$R^{11}$—$C(O)$—$R^{12}$.

$R^{11}$ can be any suitable group linking the carbonyl group to the 3-phenyl group of the compound. $R^{11}$ preferably is selected from the group consisting of alkyl groups and alkyleneoxy groups (e.g., poly(alkyleneoxy) groups). More preferably, $R^{11}$ is —$(C_2H_4O)_a(C_3H_6O)_b(C_2H_4O)_c$—, and the variables b, c, and d are integers independently selected from the group consisting of zero and the positive natural numbers, provided at least one of a, b, and c is a positive natural number. Preferably, the variables a, b, and c are independently selected from the group consisting of zero and the positive natural numbers from 1 to 100. More preferably, the variables a, b, and c are independently selected from the group consisting of zero and the positive natural numbers from 1 to 50, 1 to 20, 1 to 10, or 1 to 5. In a specific preferred embodiment, the variable a is 1, and the variables b and c are zero.

In the structure of Formula (I), the group $R^{12}$ is selected from the group consisting of hydrocarbyl groups having 25 or more carbon atoms. Preferably, the group $R^{12}$ is selected from the group consisting of hydrocarbyl groups having 27 or more carbon atoms or 29 or more carbon atoms. Suitable hydrocarbyl groups include saturated hydrocarbyl groups and unsaturated hydrocarbyl groups (i.e., hydrocarbyl groups having at least one carbon-carbon double bond). Preferably, $R^{12}$ is selected from the group consisting of hydrocarbyl groups having at least one carbon-carbon double bond. In another preferred embodiment, $R^{12}$ is selected from the group consisting of saturated hydrocarbyl groups (i.e., hydrocarbyl groups having no carbon-carbon double bonds).

In a preferred embodiment of the compound of Formula (I), $R^1$ and $R^3$ are tert-butyl groups, $R^2$, $R^4$, $R^6$, $R^7$, $R^9$, and $R^{10}$ are hydrogen, $R^8$ is —$OR^5$, $R^5$ is —$R^{11}$—$C(O)$—$R^{12}$, $R^{11}$ is —$(C_2H_4O)_a(C_3H_6O)_b(C_2H_4O)_c$—, we variable a is 1, the variables b and c are zero, and $R^{12}$ is selected from the group consisting of hydrocarbyl groups having 25 or more carbon atoms, more preferably 27 or more carbon atoms, or more preferably 29 or more carbon atoms.

In a second embodiment, the invention provides a compound comprising two or more 3-phenyl-3H-1-benzofuran-2-one moieties covalently bonded to a molecular core. In a preferred embodiment, the compound comprises two or more 3-phenyl-3H-1-benzofuran-2-one moieties and a second moiety selected from divalent and polyvalent $C_4$-$C_{60}$ hydrocarbon moieties. In such an embodiment, each 3-phenyl-3H-1-benzofuran-2-one moiety is covalently bound to an open valence of the second moiety through a linking group. In a preferred embodiment, each linking group is selected from the group consisting of a carboxy group (i.e., a group of the formula —$OC(O)$—) and oxyalkylene ester moieties. As used herein, the term "oxyalkylene ester moiety" refers to a moiety having the structure —$(OC_2H_4)_m(OC_3H_6)_n(OC_2H_4)_p$—$OC(O)$—, where the variables m, n, and p, are selected from the group consisting of zero and the positive natural numbers from 1 to 100, provided at least one of m, n, and p is a positive natural number. Preferably, the variables m, n, and p are independently selected from the group consisting of zero and the positive natural numbers from 1 to 50, 1 to 20, 1 to 10, or 1 to 5. In a specific preferred embodiment, the variable m is 1, and the variables n and p are zero.

In the compound of the second embodiment, the 3-phenyl-3H-1-benzofuran-2-one moieties can have any suitable structure. In a preferred embodiment, each 3-phenyl-3H-1-benzofuran-2-one moiety is a univalent moiety of Formula (L)

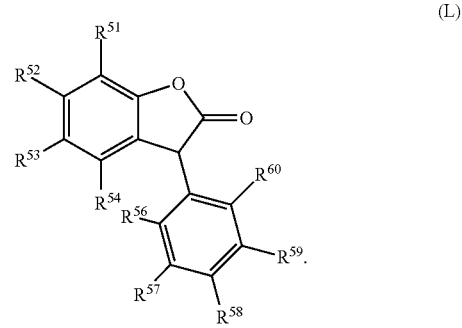

In the structure of Formula (L), $R^{51}$, $R^{52}$, $R^{53}$, and $R^{54}$ are independently selected from the group consisting of hydrogen, hydroxy, halogens, alkyl groups, substituted alkyl groups, alkoxy groups, substituted alkoxy groups, aralkyl groups, substituted aralkyl groups, alkaryl groups, substituted alkaryl groups, cycloalkyl groups, substituted cycloalkyl groups, alkylamino groups, substituted alkylamino groups, acyloxy groups, and substituted acyloxy groups. Further, adjacent pairs of $R^{51}$, $R^{52}$, $R^{53}$, and $R^{54}$ can be linked to form a fused benzene ring. $R^{56}$, $R^{57}$, $R^{58}$, $R^{59}$, and $R^{60}$ are independently selected from the group consisting of an open valence (connected to the linking group), hydrogen, halogens, alkyl groups, substituted alkyl groups, alkoxy groups, and substituted alkoxy groups, provided one of $R^{56}$, $R^{57}$, $R^{58}$, $R^{59}$, and $R^{60}$ is an open valence. Preferably, one of $R^{56}$, $R^{58}$, and $R^{60}$ is the open valence. More preferably, $R^{58}$ is the open valence.

Preferably, the compound of the second embodiment conforms to Formula (LI) or (LII)

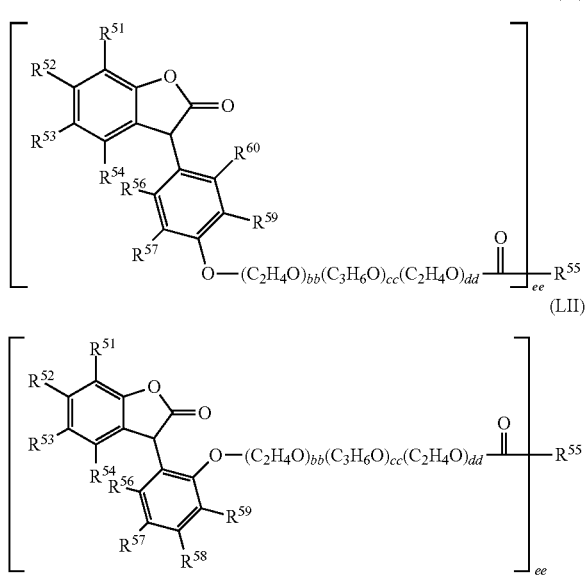

In Formulae (LI) and (LII), $R^{51}$, $R^{52}$, $R^{53}$, and $R^{54}$ are independently selected from the group consisting of hydrogen, hydroxy, halogens, alkyl groups, substituted alkyl groups, alkoxy groups, substituted alkoxy groups, aralkyl groups, substituted aralkyl groups, alkaryl groups, substituted alkaryl groups, cycloalkyl groups, substituted cycloalkyl groups, alkylamino groups, substituted alkylamino groups, acyloxy groups, and substituted acyloxy groups, provided adjacent pairs of $R^{51}$, $R^{52}$, $R^{53}$, and $R^{54}$ can be linked to form a fused benzene ring. $R^{56}$, $R^{57}$, $R^{58}$, $R^{59}$, and $R^{60}$ are independently selected from the group consisting of hydrogen, halogens, alkyl groups, substituted alkyl groups, alkoxy groups, and substituted alkoxy groups. The variables bb, cc, and dd are integers independently selected from the group consisting of zero and the positive natural numbers. The variable ee is an integer selected from the group consisting of 2 and 3. The group $R^{55}$ is selected from the group consisting of (i) hydrocarbylene groups having 18 or more carbon atoms and (ii) hydrocarbtriyl groups having 17 or more carbon atoms. As used herein, the term "hydrocarbylene" refers to divalent groups formed by removing two hydrogen atoms from a hydrocarbon (the free valences of which are not engaged in a double bond); preferably, the hydrogen atoms are removed from different carbon atoms of the hydrocarbon. As used herein, the term "hydrocarbtriyl" refers to trivalent groups formed by removing three hydrogen atoms from a hydrocarbon (the free valences of which are not engaged in a multiple bond); preferably, the hydrogen atoms are removed from different carbon atoms of the hydrocarbon.

In a preferred embodiment, $R^{51}$, $R^{52}$, $R^{53}$, and $R^{54}$ are independently selected from the group consisting of hydrogen and alkyl groups (e.g., $C_1$-$C_8$ alkyl groups, more preferably $C_1$-$C_4$ alkyl groups). More preferably, $R^{51}$ and $R^{53}$ are independently selected alkyl groups, and $R^{52}$ and $R^{54}$ are hydrogen. In such an embodiment, $R^{51}$ and $R^{53}$ preferably are tert-butyl groups.

As noted above, $R^{56}$, $R^{57}$, $R^{58}$, $R^{59}$, and $R^{60}$ are independently selected from the group consisting of hydrogen, halogens, alkyl groups, substituted alkyl groups, alkoxy groups, and substituted alkoxy groups. In a preferred embodiment, $R^{56}$, $R^{57}$, $R^{58}$, $R^{59}$, and $R^{60}$ are independently selected from the group consisting of hydrogen and alkyl groups (e.g., $C_1$-$C_8$ alkyl groups, more preferably $C_1$-$C_4$ alkyl groups). More preferably, $R^{56}$, $R^{57}$, $R^{58}$, $R^{59}$, and $R^{60}$ are hydrogen.

In a preferred embodiment, the variables bb, cc, and dd are independently selected from the group consisting of zero and the positive natural numbers from 1 to 100. In a series of preferred embodiment, the variables bb, cc, and dd are independently selected from the group consisting of zero and the positive natural numbers from 1 to 50, more preferably 0 to 20, even more preferably 0 to 10, and still more preferably 0 to 5. In a particularly preferred embodiment, the variable bb is 1, and the variables cc and dd are zero.

As noted above, $R^{55}$ is selected from the group consisting of (i) hydrocarbylene groups having 18 or more carbon atoms and (ii) hydrocarbtriyl groups having 17 or more carbon atoms. In a preferred embodiment, $R^{55}$ is selected from the group consisting of (i) hydrocarbylene groups having 22 or more carbon atoms and (ii) hydrocarbtriyl groups having 21 or more carbon atoms. More preferably, $R^{55}$ is selected from the group consisting of (i) hydrocarbylene groups having 28 or more carbon atoms and (ii) hydrocarbtriyl groups having 27 or more carbon atoms. Hydrocarbylene and hydrocarbtriyl groups suitable for $R^{55}$ can contain any practical maximum number of carbon atoms. In a preferred embodiment, the hydrocarbylene groups suitable for $R^{55}$ have no more than 50 carbon atoms or no more than 44 carbon atoms. In another preferred embodiment, the hydrocarbtriyl groups suitable for $R^{55}$ have no more than 71 carbon atoms or nor more than 67 carbon atoms. Thus, in a preferred embodiment, $R^{55}$ is selected from the group consisting of (i) hydrocarbylene groups having 18 or more carbon atoms (e.g., from 18 to 50 carbon atoms, 22 to 50 carbon atoms, 28 to 50 carbon atoms, 18 to 44 carbon atoms, 22 to 44 carbon atoms, or 28 to 44 carbon atoms) and (ii) hydrocarbtriyl groups having 17 or more carbon atoms (e.g., from 17 to 71 carbon atoms, 21 to 71 carbon atoms, 27 to 71 carbon atoms, 17 to 67 carbon atoms, 21 to 67 carbon atoms, or 27 to 67 carbon atoms).

The groups suitable for $R^{55}$ can be derived, for example, by the oligomerization of unsaturated fatty acids (fatty acids containing one or more carbon-carbon double bonds). Thus, these $R^{55}$ groups can be described as comprising linear hydrocarbyl groups (each of which originated as the hydrocarbyl moiety of a molecule of the unsaturated fatty acid) that are linked together by one or more carbon-carbon single bonds. Thus, in a preferred embodiment, $R^{55}$ is a hydrocarbylene group comprising a first $C_9$-$C_{20}$ linear hydrocarbyl group and a second $C_9$-$C_{20}$ linear hydrocarbyl group. The first $C_9$-$C_{20}$ linear hydrocarbyl group and the second $C_9$-$C_{20}$ linear hydrocarbyl group are linked by one or more carbon-carbon single bonds between a carbon atom in the first $C_9$-$C_{20}$ linear hydrocarbyl group and a carbon atom in the second $C_9$-$C_{20}$ linear hydrocarbyl group. The unsaturated fatty acids used in the oligomerization process can contain multiple carbon-carbon double bonds. In some instances, some of these carbon-carbon double bonds will not cross-link with other fatty acid molecules, which will leave carbon-carbon double bonds in the linear hydrocarbyl groups. Thus, in certain embodiments, the first $C_9$-$C_{20}$ linear hydrocarbyl group can comprise one or more carbon-carbon double bonds between adjacent carbon atoms in the first $C_9$-$C_{20}$ linear hydrocarbyl group, and the second $C_9$-$C_{20}$ linear hydrocarbyl group can comprise one or more carbon-carbon double bonds between adjacent carbon atoms in the second $C_9$-$C_{20}$ linear hydrocarbyl group. Preferably, each $C_9$-$C_{20}$ linear hydrocarbyl group is saturated and does not contain any carbon-carbon double bonds.

In a particularly preferred embodiment, the first and second $C_9$-$C_{20}$ linear hydrocarbyl groups described above are both $C_{17}$ linear hydrocarbyl groups. In such an embodiment, $R^{55}$ preferably is a group of Formula (LX), (LXI), (LXII), LXIII), (LXIV), (LXV), (LXVI), (LXVII), (LXVIII), (LXIX), or (LXX)

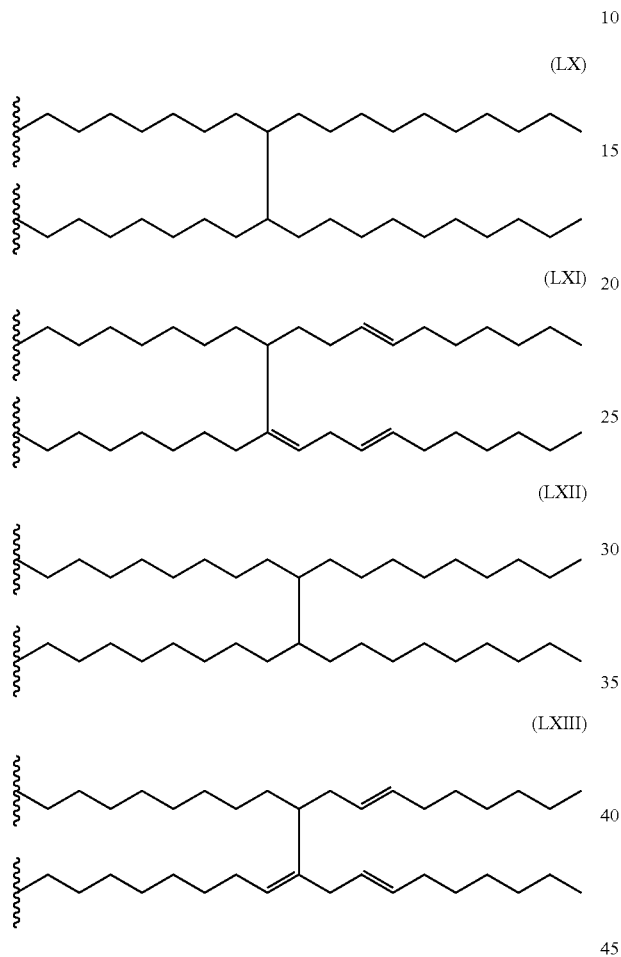
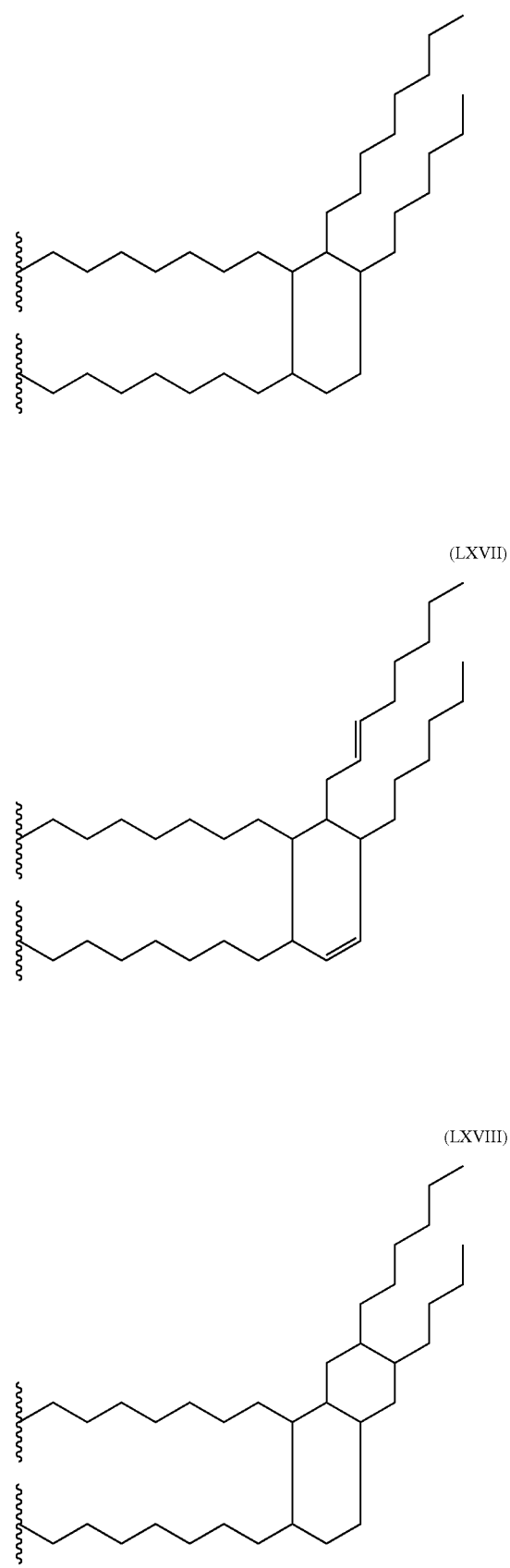

-continued (LXIX)

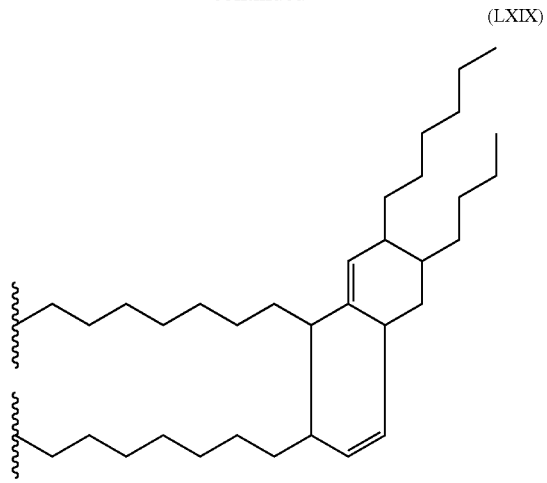

(LXX)

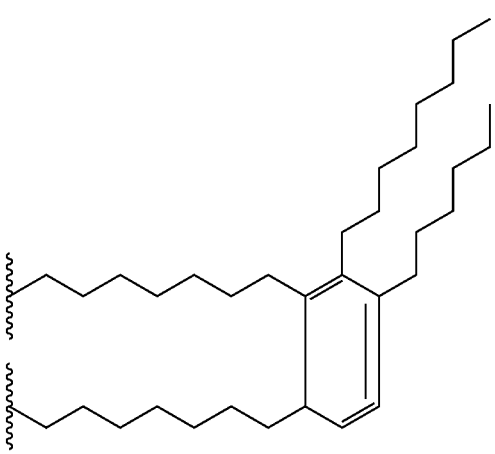

More preferably, $R^{55}$ is a group of Formula (LX), (LXII), (LXIV), (LXVI), or (LXVIII).

The compounds of the first and second embodiment can be produced by any suitable method. For example, a 3-(p-hydroxyphenyl)-3H-1-benzofuran-2-one compound or derivative thereof can be produced by reacting a phenol compound with a hydroxymandelic acid compound (e.g., 4-hydroxymandelic acid) or a hydroxymandelic acid derivative. Suitable phenol compounds include those of Formula (X)

(X)

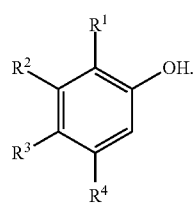

In the structure of Formula (X), the groups $R^1$, $R^2$, $R^3$, and $R^4$ are selected from any of the groups described above in connection with the compound of Formula (I). Suitable hydroxymandelic acid derivatives include those of Formula (XV)

(XV)

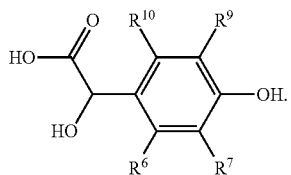

In the structure of Formula (XV), the groups $R^6$, $R^7$, $R^9$, and $R^{19}$ are selected from any of the groups described above in connection with the compound of Formula (I). The 3-(p-hydroxyphenyl)-3H-1-benzofuran-2-one compound produced by this reaction can be further reacted with the appropriate molar amount of one or more epoxides (e.g., ethylene oxide and/or propylene oxide) to add a group of formula —$(C_2H_4O)_a(C_3H_6O)_b(C_2H_4O)_cH$ onto the 3-hydroxyphenyl group. In this group, the variables a, b, and c are selected from any of the groups described above.

Alternatively, a 3-(p-hydroxyphenyl)-3H-1-benzofuran-2-one compound or derivative thereof can be produced by first reacting a first phenol compound with glyoxylic acid to produce a 3-hydroxy-3H-1-benzofuran-2-one compound. The resulting 3-hydroxy-3H-1-benzofuran-2-one compound can then be reacted with a second phenol compound or derivative thereof to produce a 3-(p-hydroxyphenyl)-3H-1-benzofuran-2-one compound or a derivative thereof. Suitable first phenol compounds include those of Formula (X) as described above. Suitable second phenol compounds include those of Formula (XX)

(XX)

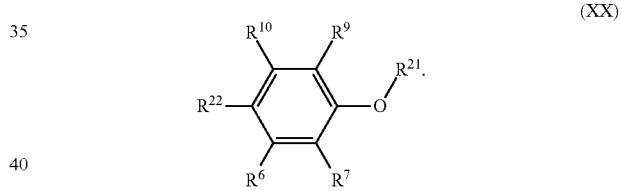

In the structure of Formula (XX), $R^6$, $R^7$, $R^9$, and $R^{16}$ are selected from any of the groups described above in connection with the compound of Formula (I), and $R^{22}$ is selected from the same groups; provided at least one of $R^7$, $R^9$, and $R^{22}$ is hydrogen. $R^{21}$ is selected from the group consisting of hydrogen and groups of the formula —$(C_2H_4O)_a(C_3H_6O)_b(C_2H_4O)_cH$, where the variables a, b, and c are selected from any of the groups described above.

Once the 3-(p-hydroxyphenyl)-3H-1-benzofuran-2-one compound or derivative thereof is obtained as described above, the compound or derivative thereof can be reacted with a suitable acyl chloride derivative of a carboxylic acid or aldehyde. This reaction produces the ester linkage described above in connection with the compounds of Formula (I) and (X). The acyl chloride can be produced from any suitable carboxylic acid or aldehyde.

In a third embodiment, the invention provides a composition comprising a compound as described above and a second component. The composition can comprise one or more compounds of Formula (I), one or more compounds of Formula (L), or a mixture of such compounds (e.g., a mixture of one or more compounds of Formula (I) and one or more compounds of Formula (L)). The second component can be any suitable plastic additive. Preferably, the second component is a solid at ambient temperature and pressure.

Second components that are solid facilitate handling and processing of the composition. Suitable second components include, but are not limited to, mineral fillers (e.g., calcium carbonate, talc, etc.), ultraviolet light absorbers (e.g., hindered amine light stabilizers), antioxidants, acid scavengers (e.g., metal salts of fatty acids), and mixtures thereof. Preferably, the second component present in the composition is selected from the group consisting of antioxidants, metal salts of fatty acids, and mixtures thereof.

In a preferred embodiment, the composition described above comprises at least one antioxidant. The antioxidant present in the composition can be any suitable antioxidant. Generally, preferred antioxidants for the composition include those that are typically used in thermoplastic polymer formulations. Preferably, the composition comprises an antioxidant selected from the group consisting of hindered phenols, aromatic amines, phosphites, and mixtures thereof. In one particularly preferred embodiment, the composition comprises a hindered phenol and a phosphite. Suitable hindered phenol antioxidants include, but are not limited to, pentaerythritol tetrakis(3-(3,5-di-tert-butyl-4-hydroxyphenyl)propionate) and octadecyl 3-(3,5-di-tert-butyl-4-hydroxyphenyl)propionate. Suitable phosphite antioxidants include, but are not limited to, tris(2,4-di-tert-butylphenyl) phosphite and bis(2,4-di-tert-butylphenol)pentaerythritol diphosphate. Suitable hindered amine antioxidants include, but are not limited to, diaryl amines (e.g., diphenylamine and derivatives thereof) and compounds (both monomeric and polymeric) containing one or more 2,2,6,6-tetraalkylpiperidinyl moieties (e.g., a 2,2,6,6-tetramethylpiperidinyl moiety). In a particularly preferred embodiment, the composition comprises, in addition to a compound of Formula (I) or Formula (L), pentaerythritol tetrakis(3-(3,5-di-tert-butyl-4-hydroxyphenyl)propionate) and tris(2,4-di-tert-butylphenyl) phosphite.

In another preferred embodiment of the composition of the third embodiment, the second component of the composition is an acid scavenger, preferably an acid scavenger that is a metal salt of a fatty acid. In such an embodiment, the composition can comprise any suitable metal salt of a fatty acid. Suitable fatty acids include saturated fatty acids and unsaturated fatty acids (e.g., monounsaturated fatty acids and polyunsaturated fatty acids). In a preferred embodiment, the fatty acid is a saturated fatty acid. In another preferred embodiment, the fatty acid is selected from the group consisting of $C_4$-$C_{28}$ fatty acids, more preferably $C_{12}$-$C_{24}$ fatty acids. In a particularly preferred embodiment, the fatty acid is stearic acid, such that the second component comprises a metal salt of stearic acid. The metal salt of the fatty acid can comprise any suitable cation. Preferably, the metal salt of the fatty acid comprises a cation selected from the group consisting of alkali metal cations, alkaline earth metal cations, and zinc cations. In a particularly preferred embodiment, the second component of the composition comprises calcium stearate, zinc stearate, or a mixture thereof.

The composition of the invention can contain any suitable amounts of the 3-phenyl-3H-1-benzofuran-2-one compound(s) described above and the second component(s). Preferably, the second component is present in the composition in an amount of about 1 part by weight or more per each part by weight of the 3-phenyl-3H-1-benzofuran-2-one compound(s) present in the composition. In another embodiment, the second component is present in the composition in an amount of about 2 parts by weight or more per each part by weight of the 3-phenyl-3H-1-benzofuran-2-one compound(s) present in the composition. In yet another embodiment, the second component is present in the composition in an amount of about 3 parts by weight or more per each part by weight of the 3-phenyl-3H-1-benzofuran-2-one compound(s) present in the composition.

The 3-phenyl-3H-1-benzofuran-2-one compound(s) described above and the compositions comprising the same (e.g., the compositions of the third embodiment) are believed to be well-suited for the stabilization of substances that are susceptible to oxidative or radical-initiated degradation. It is believed that the 3-phenyl-3H-1-benzofuran-2-one moiety scavenges radicals that are involved in the oxidative or radical-initiation processes that degrade these substances. Accordingly, in another aspect, the invention uses these 3-phenyl-3H-1-benzofuran-2-one compounds and compositions containing the same as antioxidants or stabilizers for substances that are susceptible to oxidative or radical-initiated degradation, such as organic polymers.

Thus, in a fourth embodiment, the invention provides a composition comprising an organic polymer and an additional component selected from the group consisting of a 3-phenyl-3H-1-benzofuran-2-one compound as described above, a composition as described above in the third embodiment, or a mixture thereof. The organic polymer in this fourth embodiment can be any suitable organic polymer. Preferably, the organic polymer is a thermoplastic polymer. Suitable thermoplastic polymers for the composition include, but are not limited to, polyolefins. The polyolefin polymer can be any suitable polyolefin, such as a polypropylene, a polyethylene, a polybutylene, a poly(4-methyl-1-pentene), and a poly(vinyl cyclohexane).

In a preferred embodiment, the thermoplastic polymer is polypropylene. More preferably, the thermoplastic polymer is a polyolefin selected from the group consisting of polypropylene homopolymers (e.g., atactic polypropylene homopolymers, isotactic polypropylene homopolymers, and syndiotactic polypropylene homopolymers), polypropylene copolymers (e.g., polypropylene random copolymers), polypropylene impact copolymers, and mixtures thereof. Suitable polypropylene copolymers include, but are not limited to, random copolymers made from the polymerization of propylene in the presence of a comonomer selected from the group consisting of ethylene, but-1-ene (i.e., 1-butene), and hex-1-ene (i.e., 1-hexene). In such polypropylene random copolymers, the comonomer can be present in any suitable amount, but typically is present in an amount of less than about 10 wt. % (e.g., about 1 to about 7 wt. %). Suitable polypropylene impact copolymers include, but are not limited to, those produced by the addition of a copolymer selected from the group consisting of ethylene-propylene rubber (EPR), ethylenepropylene-diene monomer (EPDM), polyethylene, and plastomers to a polypropylene homopolymer or polypropylene random copolymer. In such polypropylene impact copolymers, the copolymer can be present in any suitable amount, but typically is present in an amount of from about 5 to about 25 wt. %. The polyolefin polymers described above can be branched or cross-linked, such as the branching or cross-linking that results from the addition of additives that increase the melt strength of the polymer.

In another preferred embodiment, the thermoplastic polymer is polyethylene. In such an embodiment, the thermoplastic polymer can be any suitable polyethylene polymer. Suitable polyethylenes include, but are not limited to, low density polyethylene, linear low density polyethylene, medium density polyethylene, high density polyethylene, and combinations thereof. A description of polyethylene polymers suitable for use in the compositions of the invention can be found in U.S. Pat. No. 9,200,144 (Miley et al.), the disclosure of which is hereby incorporated by reference in its entirety.

The additional component can be present in the composition of this fourth embodiment in any suitable amount. Preferably, the additional component is present in the composition in an amount sufficient to provide about 50 ppm or more, about 75 ppm or more, or about 100 ppm or more of the 3-phenyl-3H-1-benzofuran-2-one compound. The additional component preferably is present in the composition in an amount such that the concentration of the 3-phenyl-3H-1-benzofuran-2-one compound in the composition is about 10,000 ppm or less, about 5,000 ppm or less, about 3,000 ppm or less, about 2,500 ppm or less, about 2,000 ppm or less, about 1,500 ppm or less, or about 1,000 ppm or less. Thus, in a series of preferred embodiments, the additional component is present in the composition in an amount that provides about 50 ppm to about 10,000 ppm (e.g., about 50 ppm to about 5,000, about 50 ppm to about 3,000 ppm, about 50 ppm to about 2,500 ppm, about 50 ppm to about 2,000 ppm, about 50 ppm to about 1,500 ppm, about 50 ppm to about 1,000 ppm), about 75 ppm to about 10,000 ppm (e.g., about 75 ppm to about 5,000, about 75 ppm to about 3,000 ppm, about 75 ppm to about 2,500 ppm, about 75 ppm to about 2,000 ppm, about 75 ppm to about 1,500 ppm, about 75 ppm to about 1,000 ppm), or about 100 ppm to about 10,000 ppm (e.g., about 100 ppm to about 5,000, about 100 ppm to about 3,000 ppm, about 100 ppm to about 2,500 ppm, about 100 ppm to about 2,000 ppm, about 100 ppm to about 1,500 ppm, about 100 ppm to about 1,000 ppm). If the additional component is a composition comprising two or more 3-phenyl-3H-1-benzofuran-2-one compounds, the additional component can be present in the composition in an amount such that the total amount of all 3-phenyl-3H-1-benzofuran-2-one compounds in the composition falls within one of the ranges described above, or the additional component can be present in the composition in an amount such that one or more of the 3-phenyl-3H-1-benzofuran-2-one compounds is present in an amount falling within one of the range described above. Preferably, the additional component is present in the composition in an amount such that the total amount of all 3-phenyl-3H-1-benzofuran-2-one compounds present in the composition falls within one of the ranges described above.

The polymer compositions described herein are believed to be useful in producing thermoplastic articles. The polymer compositions can be formed into the desired thermoplastic article by any suitable technique, such as injection molding, injection rotational molding, blow molding (e.g., injection blow molding or injection stretch blow molding), extrusion (e.g., sheet extrusion, film extrusion, cast film extrusion, or foam extrusion), extrusion blow molding, thermoforming, rotomolding, film blowing (blown film), film casting (cast film), and the like. The polymer compositions described herein can also be used as hot melt adhesives. In such applications, it is believed that the 3-phenyl-3H-1-benzofuran-2-one compound will be particularly useful since hot melt adhesives frequently are maintained at elevated temperatures for extended periods of time, during which they can experience significant degradation due to oxidation or other heat-induced degradation processes.

The polymer compositions described herein can be used to produce any suitable article or product. Suitable products include, but are not limited to, medical devices (e.g., pre-filled syringes, intravenous supply containers, and blood collection apparatus), food packaging, liquid containers (e.g., containers for drinks, medications, personal care compositions, shampoos, and the like), apparel cases, microwavable articles, shelving, cabinet doors, mechanical parts, automobile parts, sheets, pipes, tubes, rotationally molded parts, blow molded parts, films, fibers, and the like.

The following examples further illustrate the subject matter described above but, of course, should not be construed as in any way limiting the scope thereof.

Example 1

This example demonstrates the synthesis of a 3-phenyl-3H-1-benzofuran-2-one compound according to the invention. In particular, this example demonstrates the synthesis of 5,7-di-tert-butyl-3-[4-(2-montanoyloxyethoxy)phenyl]-benzofuran-2-one, compound (103).

Montanic acid was suspended in chloroform and stirred at 60° C. to get a clear solution. A solution of oxalyl chloride in chloroform was added dropwise. The reaction mixture was stirred at 45° C. for 2 hours, and excess oxalyl chloride and chloroform was evaporated on a vacuum rotary evaporator to give compound (303), montanoyl chloride as a white solid.

A solution of 5,7-di-tert-butyl 3-[4-(2-hydroxyethoxy) phenyl]ben-zofuran-2-one, compound (201) in chloroform was added to the flask containing the montanoyl chloride. The reaction mixture was stirred at 60° C. for 5 hours. Chloroform was removed on a vacuum rotary evaporator, and the residue was recrystallized from cold methanol to give 87% of theoretical yield of 5,7-di-tert-butyl-3-[4-(2-montanoyloxyethoxy)phenyl]-benzofuran-2-one, compound (103).

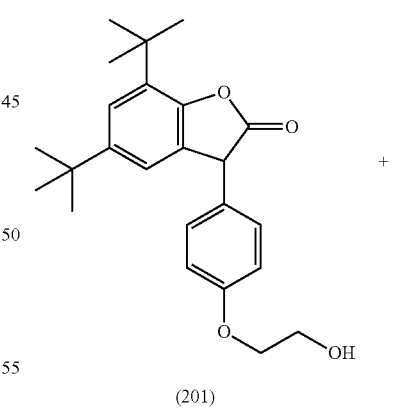

(201)

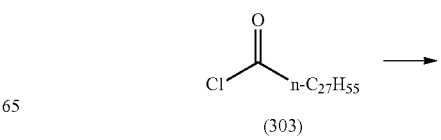

(303)

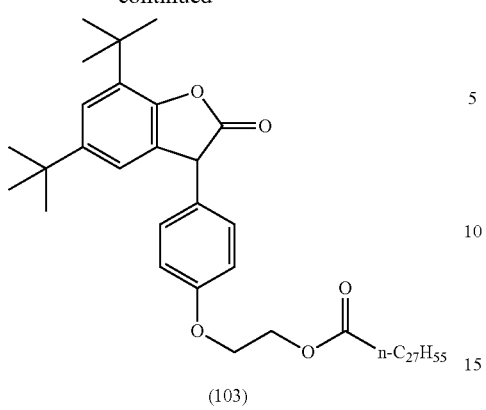

(103)

¹H-NMR (CDCl₃): 4.8 ppm (s, 1H, CH at lactone-ring); 4.4 ppm (t, 2H, CH2); 4.1 ppm (t, 2H, CH2); 2.3 ppm (t, 2H, CH2COO)

MS (LC/MS, ES negative mode): [M-1]⁻=787

Example 2

This example demonstrates the synthesis of a 3-phenyl-3H-1-benzofuran-2-one compound according to the invention.

20.00 g of UNICID™ acid 550 (m.p. 101° C., acid number 78.8 mg KOH/g) and 50 mL anhydrous toluene was added into a 250 mL round-bottomed flask with an addition funnel, a mechanical agitator, a thermocouple, and a water condenser. The reaction mixture was heated to 110° C. under agitation to get a clear solution, and then the temperature was dropped to 65° C. and maintained. 7.00 g (55 mmol) of oxalyl chloride was then added over half an hour, and the reaction mass was stirred for one more hour. Removal of excess oxalyl chloride by distillation yielded compound (305) as a white solid.

11.30 g (95%, 28.10 mmol) of 5,7-di-tert-butyl 3-[4-(2-hydroxyethoxy)phenyl]ben-zofuran-2-one, compound (201) was added to the flask containing compound (305). The reaction mixture was then refluxed at 100° C. for 8 hours. Toluene was removed on a rotary evaporator. The residue was crashed out in 700 ml of methanol under high shear mixing. The solid was collected through filtration and dried in vacuum to give 28 g (92% of theoretical yield) of compound (105) in a white solid.

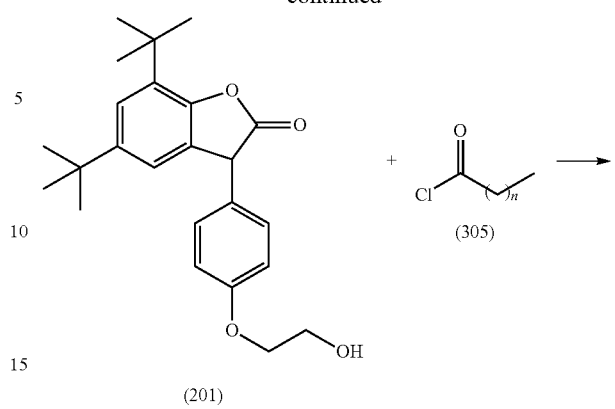

(201) (305)

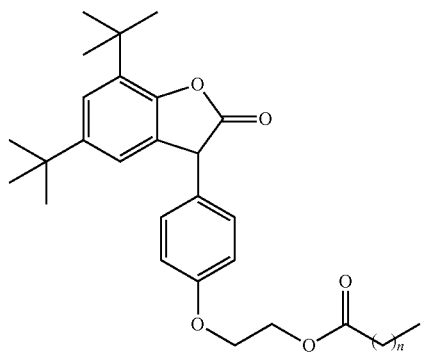

n = widely distributed
average n = 35
(105)

¹H-NMR (CDCl₃): 4.8 ppm (s, 1H, CH at lactone-ring); 4.4 ppm (t, 2H, CH2); 4.1 ppm (t, 2H, CH2); 2.3 ppm (t, 2H, CH2COO).

Example 3

This example demonstrates the synthesis of a 3-phenyl-3H-1-benzofuran-2-one compound according to the invention.

Compound (306) was prepared in similar manner to compound (305) from UNICID™ acid 700 (m.p. 110° C., acid number 63 mg KOH/g) and oxalyl chloride. Compound (106) was prepared as a white solid in a yield of 82% of theory from compound (306) and compound (201) in a similar manner to compound (105) from Example 2.

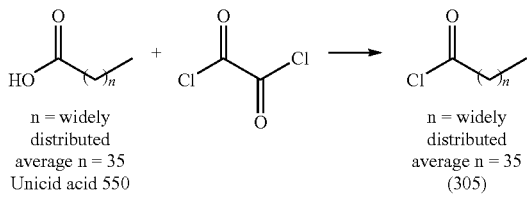

n = widely distributed
average n = 35
Unicid acid 550 n = widely distributed
average n = 35
(305)

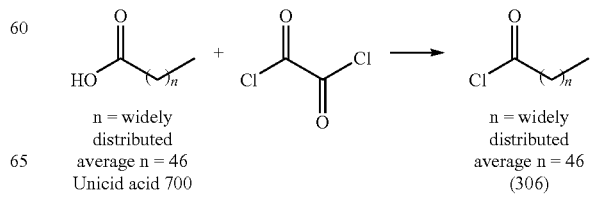

n = widely distributed
average n = 46
Unicid acid 700 n = widely distributed
average n = 46
(306)

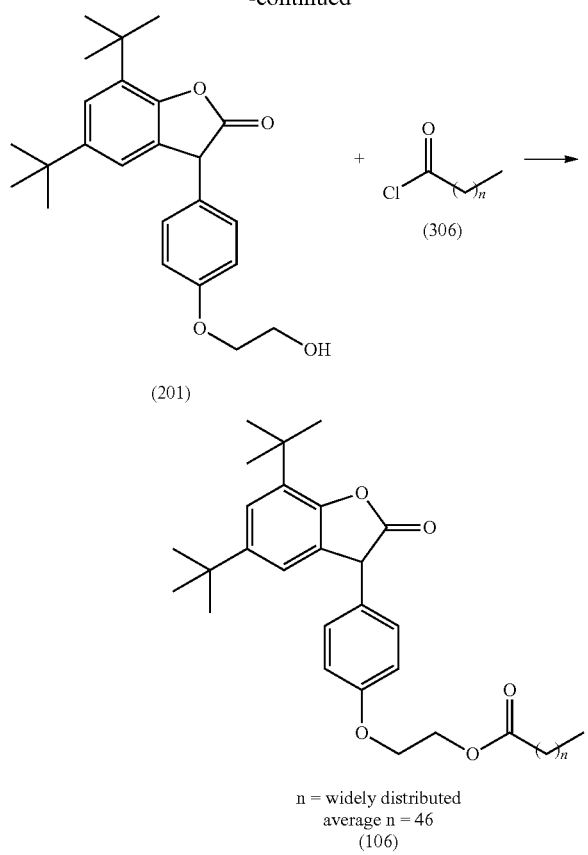

(201)

(306)

n = widely distributed
average n = 46
(106)

¹H-NMR (CDCl₃): 4.8 ppm (s, 1H, CH at lactone-ring); 4.4 ppm (t, 2H, CH2); 4.1 ppm (t, 2H, CH2); 2.3 ppm (t, 2H, CH2COO)

MS (LC/MS, ES negative mode): [M-1]⁻=1067, 1043, etc.

Example 4

This example demonstrates the synthesis of a 3-phenyl-3H-1-benzofuran-2-one compound according to the invention.

430 g (0.76 mol) of dimer acid (hydrogenated from Sigma (average mw 566)) was added to a 4 L 4-necked round bottomed flask with a mechanical agitator, a thermocouple, an addition funnel, and a water condenser. 214 g (98%, 1.65 mol) of oxalyl chloride was added over one hour while the temperature of the reaction mixture was maintained below 15° C., and then the temperature was gradually raised to 45° C. over one hour. The reaction mixture was stirred at 45° C. for another hour. Removal of excess oxalyl chloride by distillation gave dimer acid chloride, compound (307), in a liquid for the subsequent esterification without further purification.

A solution of 611 g (96%, 1.5355 mol) of 5,7-di-tert-butyl 3-[4-(2-hydroxyethoxy)phenylbenzofuran-2-one, compound (201) in 580 g of toluene was added to the flask. The reaction mixture was stirred at 85° C. for 4 hours. Toluene was removed by distillation on a rotary evaporator. The residue was crashed out in 2,000 g pre-cooled methanol at 5° C. After settling, the viscous material in the lower layer was washed with 2,000 g methanol, and the top layer was decanted. Removal of the residual methanol in the lower layer at 65° C. in vacuum gave 917.6 g (93.3% of theory) of resin-like fatty acids, C18-unsatd., dimers, hydrogenated, bis[2-[4-[5,7-bis(1,1-dimethylethyl)-2,3-dihydro-2-oxo-3-benzofuranyl]phenoxy]ethyl] esters, compound (107).

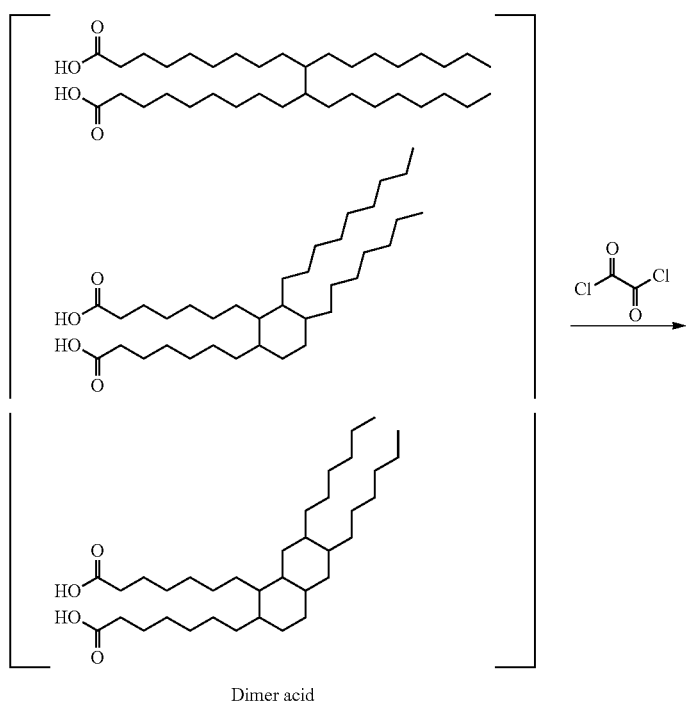

Dimer acid

-continued
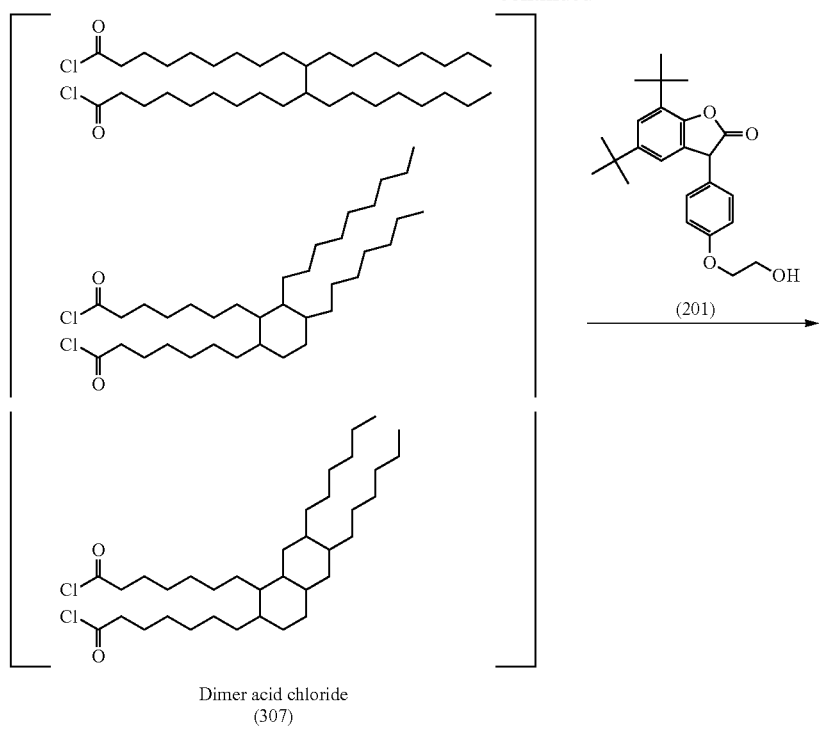
Dimer acid chloride
(307)
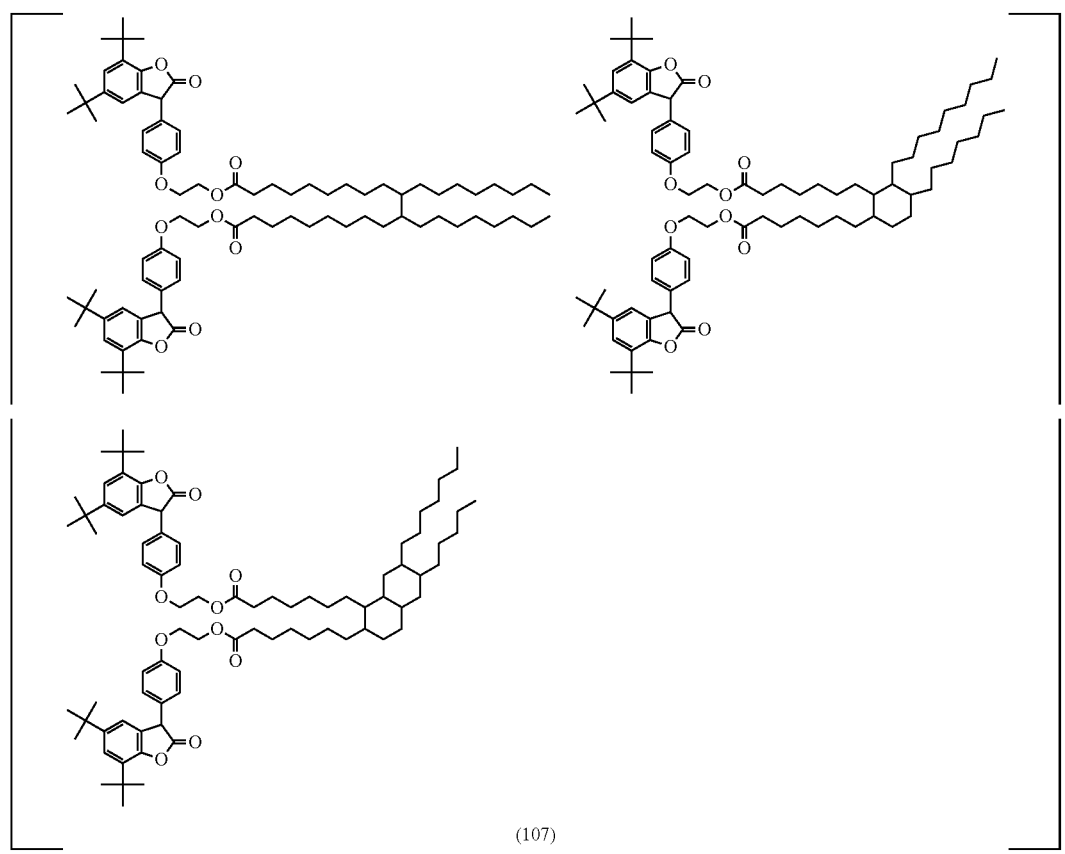
(107)

¹H-NMR (CDCl₃): 4.8 ppm (s, 2H, 2CH at lactone-ring); 4.4 ppm (t, 4H, 2CH2); 4.1 ppm (t, 4H, 2CH2); 2.3 ppm (t, 4H, 2CH2COO) MS (LC/MS, ES negative mode): [M-1]=1318, 1296, etc.

Example 5

This example demonstrates the synthesis of a 3-phenyl-3H-1-benzofuran-2-one compound according to the invention.

4.98 g (14.74 mmol) of compound (202), 5-tert-butyl-3-(2-hydroxy-5-tert-butylphenyl)benzofuran-2-one (prepared according to EP 250034 A, page 8, example 1) was dissolved in 30 g anhydrous toluene. 4.44 g of compound (307), dimer acid chloride (7.4 mmol, made as described above) was added. The reaction mixture was stirred at 85° C. for 6 hours. Toluene was removed by distillation on a rotary evaporator. The residue was washed with 40 mL methanol. After settling, the upper methanol layer was decanted. The viscous material in the lower layer was washed again with 40 mL methanol. After separation, the removal of residual methanol in the lower viscous layer at 65° C. in vacuum gave 8.67 g (yield 94% of theory) resin-like compound (108).

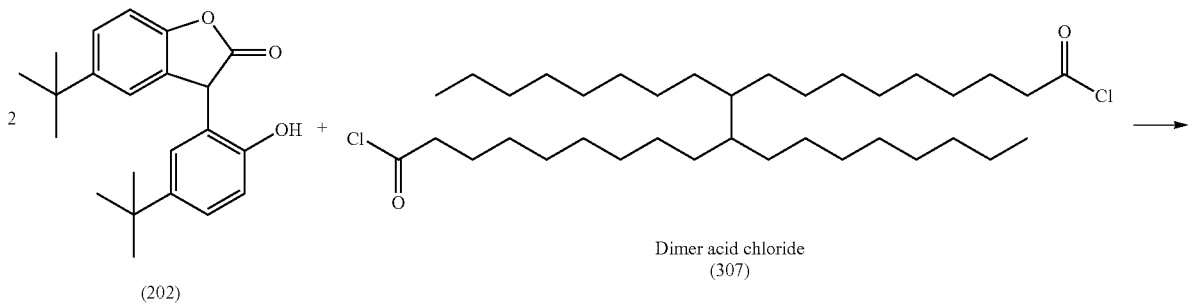

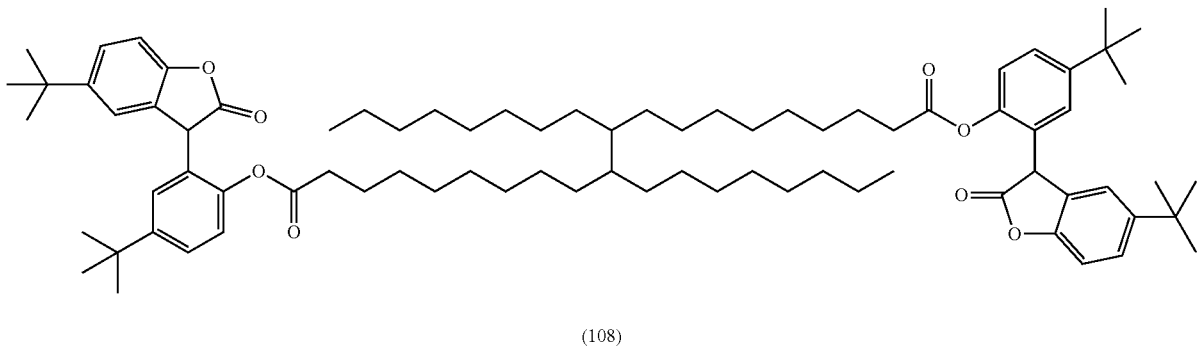

(108)

¹H-NMR (CDCl₃): 4.8 ppm (s, 2H, 2CH at lactone-ring); 2.5 ppm (t, 4H, 2CH2COO)

MS (LC/MS, ES negative mode): [M-1]⁻=1205 and 1229, etc.

Example 6

This example demonstrates the synthesis of a 3-phenyl-3H-1-benzofuran-2-one compound according to the invention.

4.98 g (14.7 mmol) of compound (203), 5,7-di-tert-butyl-3-(4-hydroxyphenyl)benzofuran-2-one (prepared according to U.S. Pat. No. 5,428,162, page 31, example 3) was dissolved in 30 g anhydrous toluene under agitation. 4.44 g (7.4 mmol) of compound (307) dimer chloride was added. The reaction mixture was stirred at 85° C. for 6 hours. Toluene was removed by distillation on a rotary evaporator. The residue was washed with 40 mL methanol. After settling, the upper methanol layer was decanted. The viscous material in the lower layer was washed again with 40 ml methanol. After separation, the removal of residual methanol in the lower viscous layer at 65° C. in vacuum gave 9.01 g (yield 97% of theory) of resin-like compound (109).

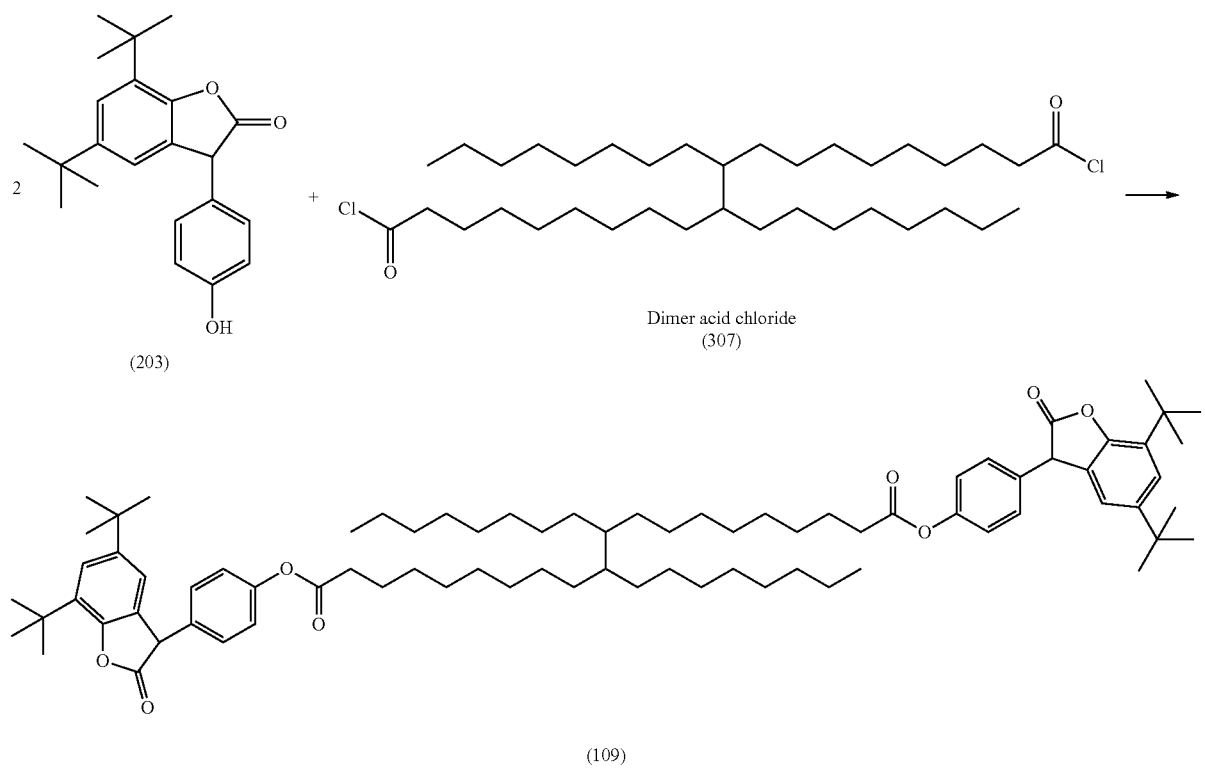

$^1$H-NMR (CDCl$_3$): 4.8 ppm (s, 2H, 2CH at lactone-ring); 2.5 ppm (t, 4H, 2CH2 at diester)

MS (LC/MS, ES negative mode): [M-1]$^-$=1205 and 1229, etc.

Example 7

This example demonstrates the production of a polymer composition according to the invention and the antioxidant properties exhibited by the 3-phenyl-3H-1-benzofuran-2-one compounds according to the invention.

Various polymer compositions were produced using a molding grade polypropylene homopolymer, Pro-fax 6301 from LyondellBasell. The formulation for the polymer compositions is set forth in Table 1 below. Irganox® B215 (from BASF) is a blend of 67 wt. % Irgafos® 168 (tris(2,4-di-tert-butylphenyl)phosphite available) and 33 wt. % of Irganox® 1010 (pentaerythritol tetrakis(3-(3,5-di-tert-butyl-4-hydroxyphenyl)propionate). "CaSt" is commercially-available calcium stearate, and "ZnSt" is commercially-available zinc stearate. Blending of the various components listed in Tables 1 and 2 was carried out with a Henschel mixer.

The blended components for each polymer composition were then subjected to six passes of extrusion in a single screw Deltaplast extruder (L:D=30) at a temperature of 260° C. The first pass was carried out under a nitrogen atmosphere to mitigate damage to the polymer due to oxidative degradation. The second to sixth passes were all extruded at a temperature of 260° C. open to air. Pelletized samples of the first, fourth, and sixth pass extrudate were collected and stored in sealed plastic bags at room temperature for later testing of the melt flow rate and yellowness index.

The melt flow rate was measured according to ASTM-1238, Procedure B on a MP-E melt index tester from Goettfert at the test conditions of 230° C. and 2.16 kg weight.

Yellowness is defined according to ASTM E31373 as the attribute by which an object color is judged to depart from a preferred white toward yellow. The yellowness index is a mathematical expression of this attribute where positive values denote yellowness and negative values denote blueness. The yellowness index of the first, fourth, and sixth passes of samples was tested to evaluate color development through successive extrusions. The yellowness index was measured on extruded pellets according to ASTM E313-73 on a Gretag Macbeth Color-Eye 7000A using illuminant C as a light source.

The results of the melt flow rate testing and the yellowness index testing are set forth in Tables 1 and 2 below.

TABLE 1

Formulation, melt flow rates, and yellowness index for Samples 1-7.

| Sample No. | 1 | 2 | 3 | 4 | 5 | 6 | 7 |
|---|---|---|---|---|---|---|---|
| HP6301 | 99.875 | 99.775 | 99.845 | 99.867 | 99.864 | 99.86 | 99.855 |
| CaSt | 0.075 | 0.075 | 0.075 | 0.075 | 0.075 | 0.075 | 0.075 |
| ZnSt | — | — | — | — | — | — | — |
| Irganox ® B215 | 0.050 | 0.150 | 0.050 | 0.050 | 0.050 | 0.050 | 0.050 |
| Compound (105) | | | 0.030 | | | | |

TABLE 1-continued

Formulation, melt flow rates, and yellowness index for Samples 1-7.

| Sample No. | 1 | 2 | 3 | 4 | 5 | 6 | 7 |
|---|---|---|---|---|---|---|---|
| Compound (107) | | | | 0.008 | 0.011 | 0.015 | 0.020 |
| Compound (108) | | | | | | | |
| Compound (109) | | | | | | | |
| Total additive content | 0.125 | 0.225 | 0.155 | 0.133 | 0.136 | 0.14 | 0.145 |
| Melt flow rates | | | | | | | |
| First pass | 15.835 | 13.74 | 14.066 | 13.649 | 14.483 | 13.973 | 14.150 |
| Fourth pass | 22.719 | 17.59 | 17.894 | 19.326 | 18.210 | 17.820 | 17.502 |
| Sixth pass | 27.812 | 20.71 | 21.061 | 22.487 | 22.168 | 20.370 | 19.966 |
| Yellowness index | | | | | | | |
| First pass | 1.597 | 0.91 | 2.546 | 1.770 | 2.591 | 2.504 | 3.321 |
| Fourth pass | 4.594 | 4.14 | 4.51 | 3.722 | 4.559 | 4.727 | 5.282 |
| Sixth pass | 6.105 | 5.69 | 5.453 | 4.863 | 5.359 | 5.769 | 6.145 |

TABLE 2

Formulation, melt flow rates, and yellowness index for Samples 8-14.

| Sample No. | 8 | 9 | 10 | 11 | 12 | 13 | 14 |
|---|---|---|---|---|---|---|---|
| HP6301 | 99.85 | 99.845 | 99.825 | 99.845 | 99.845 | 99.845 | 99.845 |
| CaSt | 0.075 | 0.075 | | | 0.075 | 0.075 | |
| ZnSt | | | 0.075 | 0.075 | | | 0.075 |
| Irganox ® B215 | 0.050 | 0.05 | 0.085 | 0.05 | 0.050 | 0.050 | 0.050 |
| Compound (105) | | | | | | | |
| Compound (107) | 0.025 | 0.030 | 0.015 | 0.030 | | | |
| Compound (108) | | | | | 0.030 | | |
| Compound (109) | | | | | | 0.030 | 0.030 |
| Total additive content | 0.150 | 0.155 | 0.175 | 0.155 | 0.155 | 0.155 | 0.155 |
| Melt flow rates | | | | | | | |
| First pass | 13.601 | 13.564 | 13.57 | 14.34 | 12.91 | 11.41 | 12.12 |
| Fourth pass | 16.723 | 16.038 | 16.76 | 17.55 | 16.37 | 14.38 | 15.12 |
| Sixth pass | 18.824 | 18.305 | 19.84 | 20.36 | 20.88 | 17.08 | 18.74 |
| Yellowness index | | | | | | | |
| First pass | 2.869 | 3.183 | 1.14 | 1.10 | 1.06 | 3.05 | 0.81 |
| Fourth pass | 5.729 | 5.694 | 4.06 | 4.04 | 4.38 | 5.76 | 3.53 |
| Sixth pass | 6.679 | 6.812 | 5.17 | 5.79 | 5.97 | 6.78 | 5.11 |

The results set forth in Tables 1 and 2 demonstrate the effectiveness of the inventive compounds as antioxidants/stabilizers for thermoplastic polymers. All the compositions containing the inventive compounds performed comparably to or better than the polymer composition containing 1,500 ppm of Irganox® B215 (Sample 2). This performance was observed for the compositions containing the inventive compounds even though the total additive content of these formulations was at least 700 ppm lower than that of Sample 2. Indeed, at a loading of only 80 ppm inventive Compound (108) delivered substantially improved melt flow rate retention and lower yellowness index than Sample 2.

The data in Tables 1 and 2 also show how acid scavenger selection can affect color development in the polymer composition. For examples, Samples 9 and 11 both contain 300 ppm of Compound (107), but Sample 11 shows a much lower yellowness index after the first pass. This difference is believed to be attributable to the use of zinc stearate in Sample 11 as opposed to the calcium stearate used in Sample 9. A similar trend is observed for Compound (109) in Samples 13 and 14 where the use of zinc stearate produced a much lower yellowness index after the first pass.

Example 8

This example demonstrates the relatively low level of extraction exhibited by the compounds of the invention.

The extraction of the compounds and some comparative compounds was evaluated using a modified FDA method at 100° C. In the modified method, extruded films are used instead of injection molded plaques to speed up the extraction rate. The extracted compound in 50% ethanol is hydrolyzed to give compound (201), a free lactone compound. The extracted concentration (ppm) in 50% ethanol is reported based on the quantification on compound (201).

The films used in the extraction tests were prepared from the formulation set forth in Table 3 below. The components of each formulation were first blended in a coffee grinder and then extruded into films on a Randcastle RCP-0375 Microtruder with a temperature profile of 165/195/205/215° C. and a screw speed of 119 rpm. In addition to inventive compounds (103), (105), (106), and (107), comparative compounds (101), (102), and (104) having the structures below were also tested.

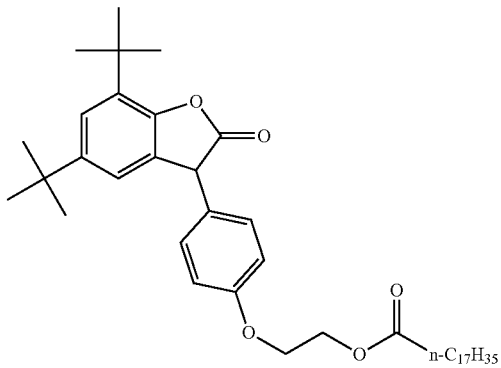

(101)

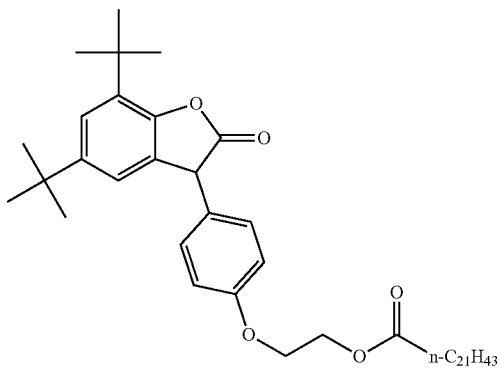

(102)

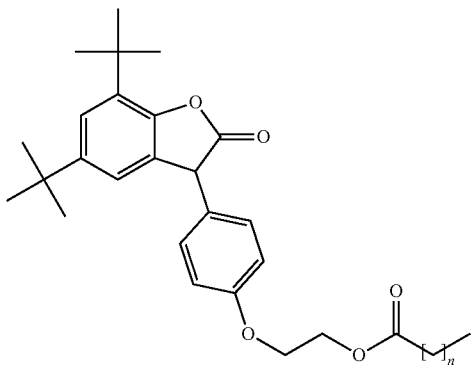

(104)

where n is distributed with an average value of 21.

TABLE 3

| General formulation for films used in extraction testing. | | | |
|---|---|---|---|
| HP6301 | ZnSt | Irganox B215 | Evaluated compound |
| 99.845 parts | 0.075 parts | 0.050 parts | 0.030 parts |

The results of the extraction testing are set forth in Table 4 below.

TABLE 4

| Results of the extraction testing. | | | | |
|---|---|---|---|---|
| Evaluated Compound | Molecular weight/mol lactone | Relative moles of lactone | Extracted concentration (ppm) in 50% ethanol | Relative extractability/ mol lactone |
| Compound (101) | 648 | 0.463 | 2.170 | 4.687 |
| Compound (102) | 704 | 0.426 | 1.158 | 2.718 |
| Compound (103) | 788 | 0.381 | 0.627 | 1.646 |
| Compound (104) | 724 | 0.414 | 1.081 | 2.611 |
| Compound (105) | 1074 | 0.279 | 0.525 | 1.881 |
| Compound (106) | 1253 | 0.239 | 0.391 | 1.636 |
| Compound (107) | 648 | 0.463 | 0.281 | 0.607 |

As can be seen in Table 4, the compounds (103), (105), (106), and (107) each exhibited relative extractability values below 2. The low relative extractability values exhibited by these compounds is believed to be attributable to the relatively long hydrocarbon chains attached to the 3-phenyl group of the compounds. By way of contrast, compounds (101), (102), and (104), each of which possessed a relatively shorter hydrocarbon group on the 3-phenyl group, exhibited relative extractability values greater than 2. These differences in extractability are surprising given the fact that the average length of the hydrocarbon group for compounds (104) and (103) only differed by five carbons.

Example 9

This example demonstrates the antioxidant properties exhibited by the compounds of the invention in polyethylene.

Two polymer compositions were produced using a molding grade low-density polyethylene, NA 2170000. The formulation for the polymer compositions is set forth in Table 5 below. Blending of the various components listed in Table 5 was carried out with a Henschel mixer. The mixtures were extruded into pellets in a single screw Deltaplast extruder (L:D=30) at a temperature profile of 160/175/190/190/190/190° C. The 2"×3" plaques with a thickness of 50 mil were molded for determining oxidative induction time (OIT). Oxidative induction time was measured by differential scanning calorimetry (DSC) at 185° C. based on ASTM E1858-08.

TABLE 5

| Formulation for Samples 9A and 9B. | | | |
|---|---|---|---|
| Sample | Polymer | ZnSt | Irganox B215 Inventive Compound |
| 9A | 99.950 parts | — | 0.050 parts — |
| 9B | 99.825 parts | 0.075 parts | 0.050 parts 0.050 parts |

TABLE 6

Results of OIT Testing

| Sample | OIT at 185° C. (min.) |
|---|---|
| 9A | 14 |
| 9B | 59 |

The polymer composition containing only Irganox B215 and none of the inventive compounds (Sample 9A) exhibited an OIT of 14 minutes. The polymer composition containing a compound of the invention (Sample 9B) exhibited an OIT of 59 minutes, which is over four times the OIT of Sample 9A. These data show the efficacy of the inventive compounds as antioxidants in polyethylene.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A compound comprising two or more 3-phenyl-3H-1-benzofuran-2-one moieties and a second moiety selected from the group consisting of divalent and polyvalent $C_4$-$C_{60}$ hydrocarbon moieties, wherein each 3-phenyl-3H-1-benzofuran-2-one moiety is covalently bound to an open valence of the second moiety through a linking group selected from the group consisting of a carboxy group and oxyalkylene ester moieties, and the compound conforms to Formula (LI) or (LII)

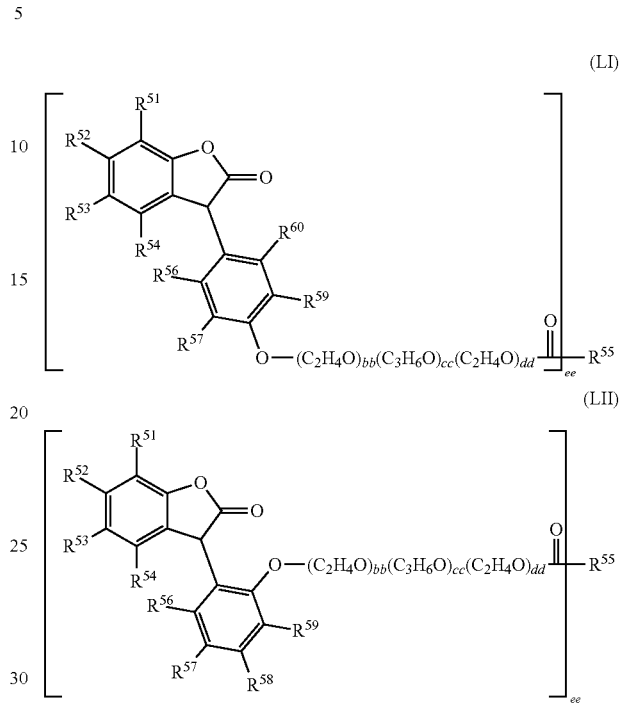

wherein $R^{51}$, $R^{52}$, $R^{53}$, and $R^{54}$ are independently selected from the group consisting of hydrogen, hydroxy, halogens, alkyl groups, substituted alkyl groups, alkoxy groups, substituted alkoxy groups, aralkyl groups, substituted aralkyl groups, alkaryl groups, substituted alkaryl groups, cycloalkyl groups, substituted cycloalkyl groups, alkylamino groups, substituted alkylamino groups, acyloxy groups, and substituted acyloxy groups, provided adjacent pairs of $R^{51}$, $R^{52}$, $R^{53}$, and $R^{54}$ can be linked to form a fused benzene ring; $R^{56}$, $R^{57}$, $R^{58}$, $R^{59}$, and $R^{69}$ are independently selected from the group consisting of hydrogen, halogens, alkyl groups, substituted alkyl groups, alkoxy groups, and substituted alkoxy groups; the variables bb, cc, and dd are integers independently selected from the group consisting of zero and the positive natural numbers; the variable ee is an integer selected from the group consisting of 2 and 3; and $R^{55}$ is selected from the group consisting of (i) hydrocarbylene groups having 18 or more carbon atoms and (ii) hydrocarbtriyl groups having 17 or more carbon atoms.

2. The compound of claim 1, wherein $R^{51}$ and $R^{53}$ are independently selected from the group consisting of alkyl groups, and $R^{52}$ and $R^{54}$ are hydrogen.

3. The compound of claim 1, wherein $R^{51}$ and $R^{53}$ are each tert-butyl.

4. The compound of claim 1, wherein $R^{56}$, $R^{57}$, $R^{58}$, $R^{59}$, and $R^{69}$ are hydrogen.

5. The compound of claim 1, wherein the variables bb, cc, and dd are independently selected from the group consisting of zero and the positive natural numbers from 1 to 100.

6. The compound of claim 1, wherein the variable bb is 1, and the variables cc and dd are zero.

7. The compound of claim 1, wherein $R^{55}$ is selected from the group consisting of (i) hydrocarbylene groups having 28 or more carbon atoms and (ii) hydrocarbtriyl groups having 27 or more carbon atoms.

8. The compound of claim 1, wherein $R^{55}$ is a hydrocarbylene group comprising a first $C_9$-$C_{20}$ linear hydrocarbyl group and a second $C_9$-$C_{20}$ linear hydrocarbyl group, the first $C_9$-$C_{20}$ linear hydrocarbyl group and the second $C_9$-$C_{20}$ linear hydrocarbyl group being linked by one or more carbon-carbon single bonds between a carbon atom in the first $C_9$-$C_{20}$ linear hydrocarbyl group and a carbon atom in the second $C_9$-$C_{20}$ linear hydrocarbyl group.

9. The compound of claim 8, wherein the first $C_9$-$C_{20}$ linear hydrocarbyl group and the second $C_9$-$C_{20}$ linear hydrocarbyl group are each saturated hydrocarbyl groups.

10. The compound of claim 8, wherein the first $C_9$-$C_{20}$ linear hydrocarbyl group is a $C_{17}$ linear hydrocarbyl group and the second $C_9$-$C_{20}$ linear hydrocarbyl group is a $C_{17}$ linear hydrocarbyl group.

11. The compound of claim 1, wherein $R^{55}$ is a group of Formula (LX), (LXI), (LXII), LXIII), (LXIV), (LXV), (LXVI), (LXVII), (LXVIII), (LXIX), or (LXX)

(LX)

(LXI)

(LXII)

(LXIII)

(LXIV)

(LXV)

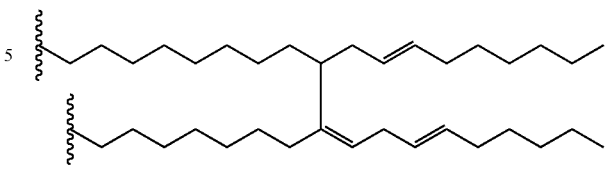

(LXVI)

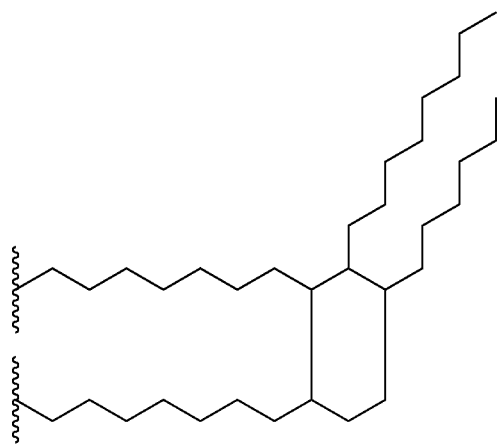

(LXVII)

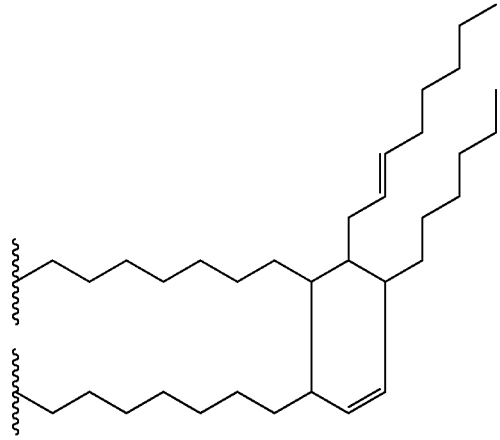

(LXVIII)

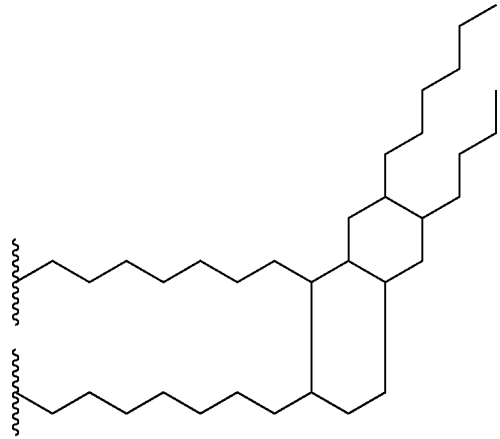

-continued

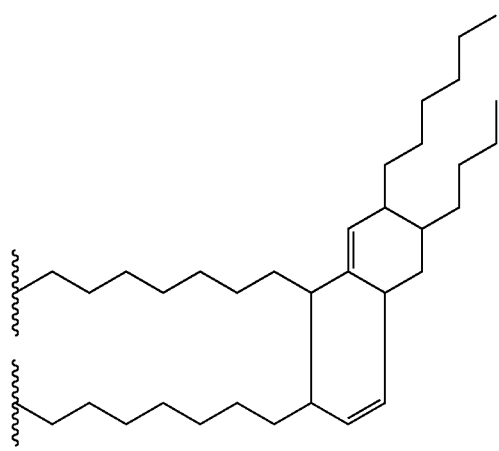
(LXIX)

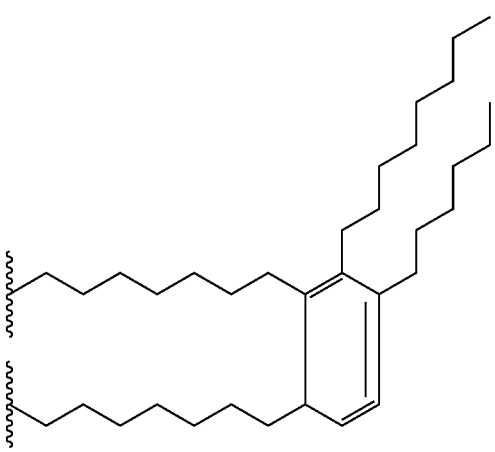
(LXX)

12. A composition comprising a compound of claim 1 and a second component selected from the group consisting of fillers, ultraviolet light absorbers, antioxidants, acid scavengers, and mixtures thereof.

13. The composition of claim 12, wherein second component is an antioxidant selected from the group consisting of hindered phenols, aromatic amines, phosphites, and mixtures thereof.

14. The composition of claim 13, wherein the composition comprises a hindered phenol and a phosphite.

15. The composition of claim 12, wherein the composition comprises an acid scavenger, and the acid scavenger is a metal salt of a fatty acid.

16. The composition of claim 15, wherein the second component is a metal salt of a $C_4$-$C_{28}$ fatty acid.

17. The composition of claim 15, wherein the second component is a metal salt of a $C_{12}$-$C_{24}$ fatty acid.

18. The composition of claim 15, wherein the second component is a metal salt of stearic acid.

19. The composition of claim 15, wherein the metal salt of a fatty acid comprises a cation selected from the group consisting of alkali metal cations, alkaline earth metal cations, and zinc cations.

20. The composition of claim 15, wherein the second component is zinc stearate.

21. A composition comprising an organic polymer and a compound of claim 1.

22. The composition of claim 21, wherein the organic polymer is a polyolefin.

23. The composition of claim 22, wherein the polyolefin is a polypropylene.

24. The composition of claim 22, wherein the polyolefin is a polyethylene.

* * * * *